United States Patent
Fukuzono et al.

(10) Patent No.: US 6,409,380 B1
(45) Date of Patent: Jun. 25, 2002

(54) DEW FORMATION PREDICTION METHOD AND APPARATUS, ENVIRONMENT AIR TEMPERATURE ESTIMATING METHOD AND APPARATUS AND RECORDING AND/OR REPRODUCING APPARATUS

(75) Inventors: Seiichi Fukuzono, Kanagawa; Kenichi Michitaka, Tokyo, both of (JP)

(73) Assignee: Sony Precision Technology Inc., Tokyo (JP)

( * ) Notice: Subject to any disclaimer, the term of this patent is extended or adjusted under 35 U.S.C. 154(b) by 0 days.

(21) Appl. No.: 09/558,737

(22) Filed: Apr. 26, 2000

(30) Foreign Application Priority Data

Apr. 27, 1999 (JP) .............................. 11-120245

(51) Int. Cl.$^7$ ......................... G01N 25/66; G01N 25/12
(52) U.S. Cl. ................................. 374/28; 73/73; 374/16
(58) Field of Search .............................. 374/16, 27, 28; 73/73

(56) References Cited

U.S. PATENT DOCUMENTS

| | | | | |
|---|---|---|---|---|
| 3,612,376 A | * | 10/1971 | Johnson | ...................... 226/194 |
| 4,257,076 A | * | 3/1981 | Shimizu et al. | ......... 360/130.24 |
| 4,272,986 A | * | 6/1981 | Lowry et al. | ................... 73/73 |
| 4,378,168 A | * | 3/1983 | Kuisma et al. | ................ 374/28 |
| 4,506,994 A | * | 3/1985 | Schwab | ........................ 374/28 |
| 5,741,067 A | * | 4/1998 | Gschwind et al. | ............. 374/16 |

FOREIGN PATENT DOCUMENTS

| JP | 363233357 | * 9/1988 | .................. 374/27 |
|---|---|---|---|

* cited by examiner

Primary Examiner—Diego Gutierrez
Assistant Examiner—Gail Verbitsky
(74) Attorney, Agent, or Firm—Jay H. Maioli

(57) ABSTRACT

A dew formation occurrence detection apparatus for detecting the dew formation on a drum 4 of a tape transport system provided on the electronic equipment 1 as an object for measurement. The dew formation occurrence detection apparatus includes a drum temperature detection unit 8 for detecting the temperature of the drum 4, an environment air temperature acquisition unit 6 for acquiring the environment air temperature of the electrical equipment 1 and a dew point temperature calculating unit 6 for calculating, from this environment air temperature, the dew point temperature at the humidity which takes the operating environment of the electronic equipment 1 into account. When the temperature of the drum 4 is not higher than this dew point temperature, it is verified that dew formation has occurred.

9 Claims, 3 Drawing Sheets

DEW FORMATION PREDICTION METHOD AND APPARATUS, ENVIRONMENT AIR TEMPERATURE ESTIMATING METHOD AND APPARATUS AND RECORDING AND/OR REPRODUCING APPARATUS

BACKGROUND OF THE INVENTION

1. Field of the Invention

This invention relates to a dew formation prediction method and apparatus, and an environment air temperature estimating method and apparatus, which may conveniently be used for estimating the environment air temperature by a temperature sensor provided in an electronic equipment and for predicting the dew formation on an object under measurement provided in the electronic equipment.

2. Description of Related Art

If, in an object under measurement, such as a drum, of a tape transport system of a helical scanning system, provided in an electronic equipment, such as a data recorder or a video tape recorder, dew is produced, the magnetic tape may stick to the drum and thereby is unable to run, while there is a risk of the magnetic tape being damaged seriously.

Up to now, a dew formation sensor is provided for this drum and, when the dew formation is detected by this dew formation sensor, air is blown onto this drum by e.g., an air blowing fan, whilst the apparatus is allowed to stand until the dew drops have disappeared.

Meanwhile, the conventional dew formation sensor checks the dew formation based on changes in the resistance of the due formation sensor. However, changes in the resistance in the vicinity of the dew point temperature are extremely small so that it is difficult to verify whether or not the dew formation has actually occurred.

When a data recorder is used outdoors to record measurement data on magnetic tape using a tape transport system with the helical scan system and then brought indoors to reproduce the measurement data, there are cases where dew drops are formed on the drum surface but the change in resistance of the due formation sensor is so small that the sensor falls to respond to that change, giving an incorrect decision.

For eliminating such mistaken decisions, it is necessary to approximate the ambient environment of the dew sensor to that of the drum. In particular, in an electronic equipment in which forced convection is used for heat dissipation, limitations are placed on the mounting position of the dew formation sensor.

Moreover, in order for the dew formation sensor to detect the dew formation on the drum reliably, the thermal capacity of the dew formation sensor needs to be equal to that of the drum, such that a sufficient space is required around the dew formation sensor and hence the space saving demand is not met.

SUMMARY OF THE INVENTION

It is therefore an object of the present invention to provide a method and apparatus for detecting the temperature of the environment air around the electronic equipment and an object under measurement mounted in the electronic equipment to predict dew formation satisfactorily.

In one aspect, the present invention provides a dew formation prediction apparatus including object temperature detection means for detecting the temperature of an object provided in an electronic equipment, environment air temperature acquiring means for acquiring the environment air temperature surrounding the electronic equipment, dew point temperature calculating means for calculating the dew point temperature at a humidity which takes the operating environment around the electronic equipment into account, from the environment air temperature, and dew formation occurrence verification means for verifying the occurrence of dew formation when the temperature of the object as acquired by the object temperature detection means is not higher than the dew point temperature.

In another aspect, the present invention provides a dew formation prediction method including detecting the temperature of an object provided in an electronic equipment, acquiring the environment air temperature of the electronic equipment, calculating the dew point temperature at a humidity which takes the operating environment around the electronic equipment into account, from the environment air temperature, and verifying the occurrence of dew formation when the temperature of the object is not higher than the dew point temperature.

In still another aspect, the present invention provides an environment air temperature estimating apparatus including temperature measurement means for measuring the temperature $T_0$ on powerup of an object under measurement provided in an electronic equipment and the temperature $T_1$ of the object under measurement after lapse of a pre-set time as from powerup and environment air temperature calculating means for calculating the environment air temperature $T_E$ from $$T_E = AT_1 - BT_0 - C$$

where $T_0$ is the temperature on powerup of the object under measurement as obtained by the object temperature measurement means, $T_1$ is the temperature of the object under measurement after lapse of a specified time period as from powerup, A and B are coefficients to compensate for the variations in the ambient environment inside and outside the electronic equipment and C is a constant representing the environment air temperature $T_E$ when $AT_1$ and $BT_0$ representing the temperatures of the object under measurement when taking into account the conditions of the environment inside and outside the electronic equipment are equal to each other.

In still another aspect, the present invention provides an environment air temperature estimating method including measuring the temperature $T_0$ on powerup of an object under measurement provided in an electronic equipment and the temperature $T_1$ of the object under measurement after lapse of a pre-set time as from the and calculating the environment air temperature $T_E$ from $$T_E = AT_1 - BT_0 - C$$

where $T_0$ is the temperature as measured on powerup of the object under measurement, $T_1$ is the temperature of the object under measurement after lapse of a specified time period as from powerup, A, B are coefficients to compensate for the variations in the conditions of the ambient environment inside and outside the electronic equipment and C is a constant representing the environment air temperature $T_E$ when $AT_1$ and $BT_0$ representing the temperatures of the object under measurement when taking into account the conditions of the environment inside and outside the electronic equipment are equal to each other.

In yet another aspect, the present invention provides a recording and/or reproducing apparatus of a helical scan system having a tape transport system, including drum temperature detection means for detecting the temperature of a drum of the tape transport system provided in a main body of the apparatus, environment air acquisition means for acquiring the environment air temperature around the main body of the apparatus, dew point temperature calculating means for calculating, from the environment air temperature, the dew point temperature at a humidity which takes into account the operating temperature around the main body of the apparatus, and dew formation occurrence verification means for verifying the occurrence of dew formation when the drum temperature as obtained by the drum temperature detection means is not higher than the dew point temperature.

According to the present invention, detection of the temperature of an object set in an electronic equipment and estimation of the environment air temperature around the electronic equipment can be achieved using a sole temperature sensor to enable dew formation to be predicted satisfactorily.

That is, according to the present invention, the environment air temperature can be estimated by providing a sole temperature sensor adapted to measure the temperature of an object provided in the electronic equipment. The measured results can be used to predict the dew formation satisfactorily.

Moreover, according to the present invention, since a sole temperature sensor is provided in the electronic equipment for measuring the object temperature, there is no risk of wastefully consuming the space available in the electronic equipment.

DESCRIPTION OF THE PREFERRED EMBODIMENTS

Figure 1:
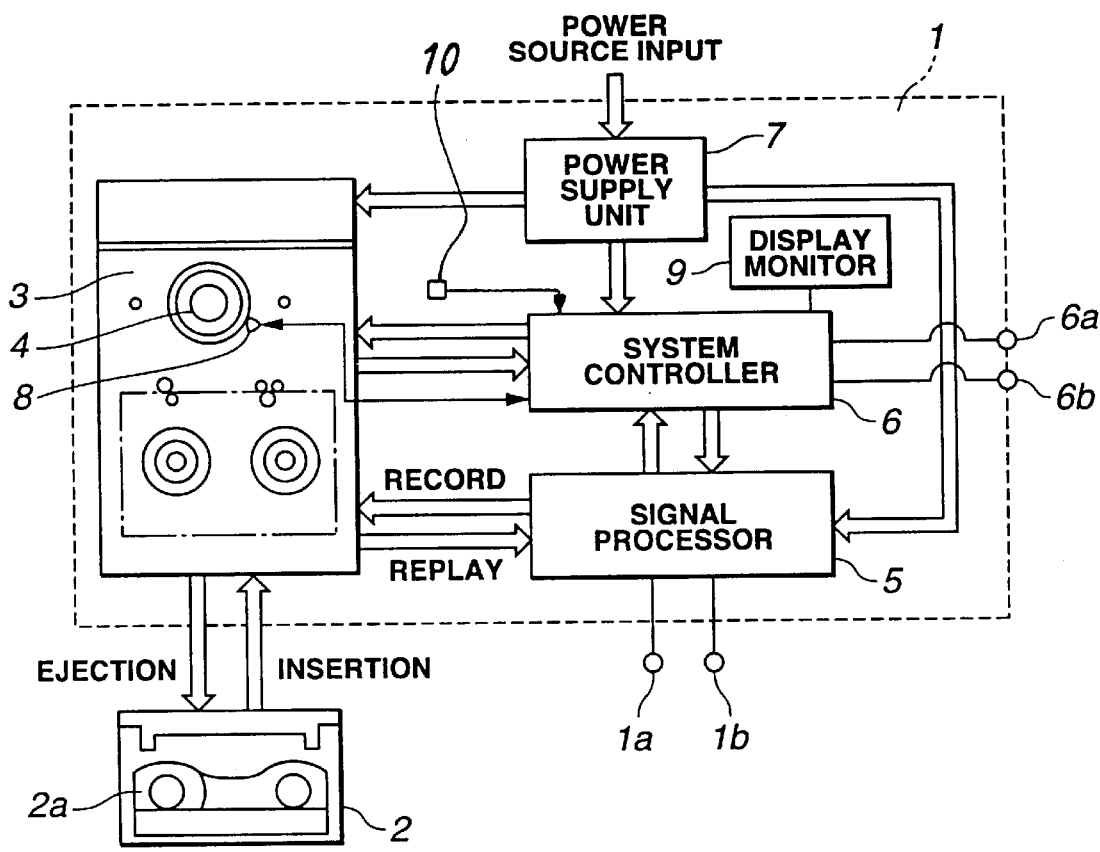
FIG. 1 is a schematic view showing an illustrative structure of a data recorder embodying the present invention.

Referring to the drawings, preferred embodiments of the present invention will be explained in detail.

Figure 3:
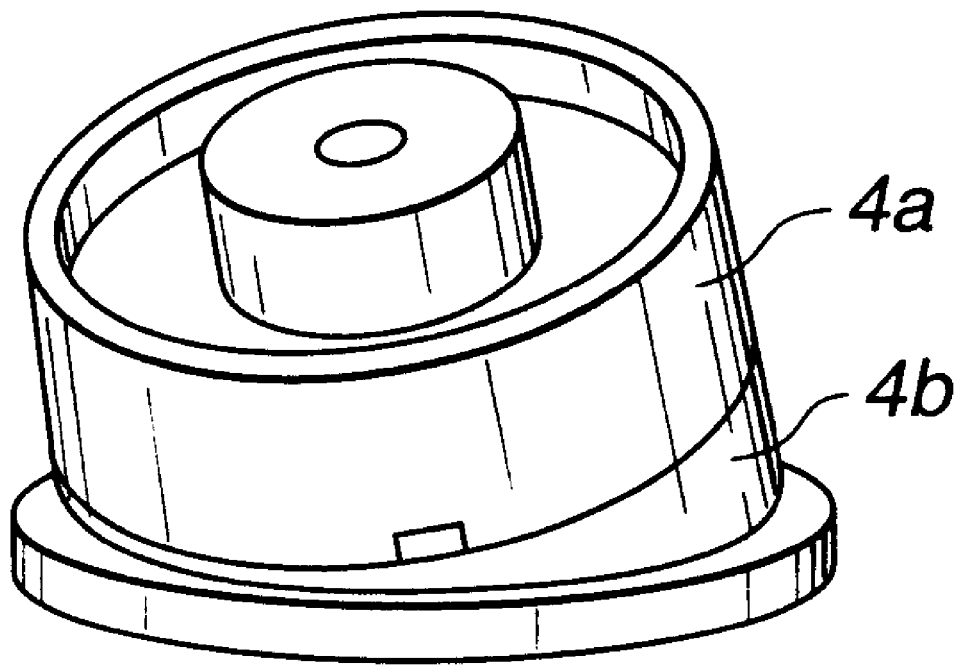
FIG. 3 is a perspective view showing an example of a drum in the tape recorder.

Referring to FIGS. 1 and 3, an illustrative configuration of a dew formation prediction device embodying the present invention is explained. FIG. 1 shows the dew formation prediction device of the present invention as applied to the data recorder.

In FIG. 1, 1 denotes a data recorder in its entirety. Within this data recorder 1, there is provided a cassette tape operating unit 3 of a tape transport system employing a helical scan system in which data is recorded on a magnetic tape 2a loaded on the tape cassette 2 and the data recorded on the magnetic tape 2a loaded on the tape cassette 2 is reproduced.

This cassette tape operating unit 3 includes a drum 4 of the helical scanning configuration for winding the magnetic tape 2a thereon and for recording and/or reproducing the data by a rotary head. Referring to FIG. 3, the drum 4 is made up of an upper drum 4a and a lower drum 4b, with the upper drum 4a carrying a head, as shown in FIG. 3. The upper drum 4a is rotatable, with the lower drum 4b being stationary. Of, course, the disposition of the upper and lower drums may be reversed, that is the lower drum 4b and the upper drum 4a may be rotatable and stationary, respectively.

This cassette tape transport unit 3 is arranged so that the tape cassette 2 with the magnetic tape 2a loaded therein can be inserted in position and ejected as necessary.

Also, in FIG. 1, data from a data input terminal 1a is sent to a signal processor 5 where pre-set signal processing occurs. The processed signals are routed as a recording signal to the cassette tape transport unit 3 so as to be recorded on the magnetic tape 2a of the tape cassette 2.

Also, playback signals reproduced by the cassette tape transport unit 3 of the helical scan system are routed through the signal processor 5 to an output terminal 1b. The playback data signals, obtained from the output terminal 1b, are sent, for example, to a computer, for observation and analysis.

In FIG. 1, 6 denotes a system controller made up of a micro-computer adapted for controlling the data recorder 1. This system controller 6 controls the operations, such as recording and/or reproducing operations, of the cassette tape operating unit 3, while controlling the signal processor 5 in a specified manner.

6a, 6b denote an input terminal and an output terminal for communication of control signals between the system controller 6 and the outside, respectively. The data recorder 1 is adapted for being controlled by control signals from outside through the input terminal 6a and the output terminal 6b.

7 denotes a power source unit for producing the power which is routed to the cassette tape operating unit 3, system controller 6 and to the signal processor 5.

In the present embodiment, there is provided a temperature sensor 8 for detecting the temperature of the drum 4 of the cassette tape operating unit 3 of the helical scan system. The temperature sensor 8 may be provided on, for example, the lower drum 4b of the drum 4. In this case, the temperature of the drum 4 can be measured directly.

Figure 2:
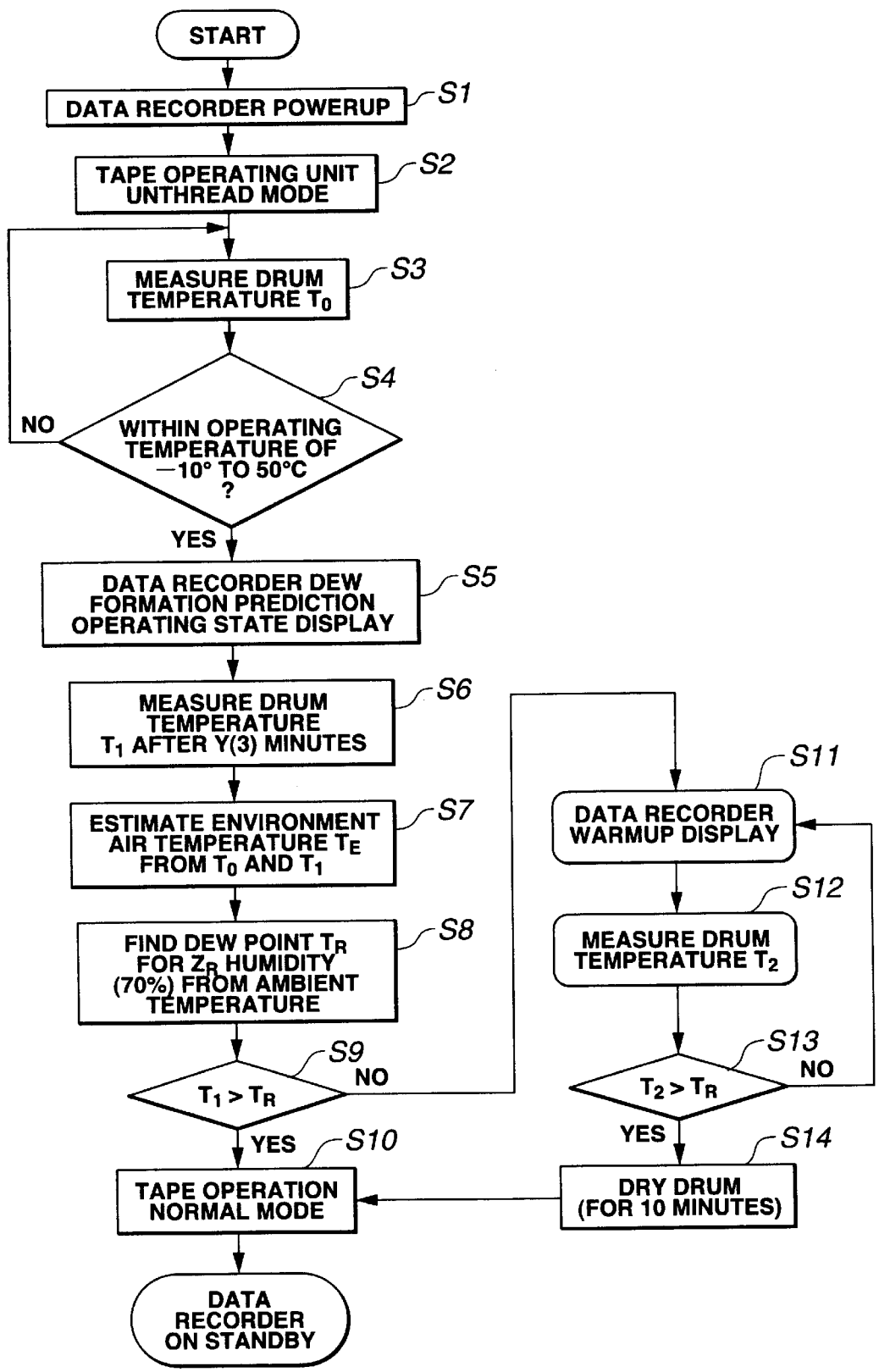
FIG. 2 is a flowchart for illustrating the present invention.

The detected temperature value of the drum 4, obtained by the temperature sensor 8, is routed to the system controller 6, which then predicts the dew formation on the drum 4, by the temperature of the drum 4, in accordance with the flowchart shown in FIG. 2.

9 denotes a display monitor configured for displaying the progress and the state when the system controller 6 has verified the occurrence of dew formation and during the warmup and for making usual data recorder display when the data recorder 1 is in the standby state.

Referring to FIG. 2, an example of predicting dew formation on the drum 4 of the cassette tape operating unit 3 of the helical scan system provided in the data recorder 1 is explained.

First, the power source of the data recorder 1 is turned on at step S1. At this time, the recorder is set to the "unthread" mode, in which the drum 4 of the cassette tape operating unit 3 of the present data recorder 1 is run but the magnetic tape 2a is not in contact with the drum 4 (step S2).

The temperature $T_0$ on powerup of the drum 4 is measured by the temperature sensor 8 (step S3). It is then verified whether or not the temperature $T_0$ of the drum 4 is appropriate for using the data recorder 1, for example, within a range from −10° C. to 50° C. (step S4). If the temperature $T_0$ of the drum 4 is outside the temperature range suited for use, the drum 4 is allowed to stand by as it is heated or cooled until the temperature $T_0$ of the drum 4 reaches the temperature suited for use. When the temperature $T_0$ of the drum 4 is found to be in the range outside of −10° C. to +50° C., the display monitor 9 flashes "LOT WAIT" for the temperature range lower than −10° C. and "HIT WAIT" for the temperature range higher than +50° C. When the temperature $T_0$ is found to be in the range of −10° C. to +50° C., the display monitor 9 shows the countdown 180 s to 000 s, indicating the time set before measuring the temperature of the drum 4 again (step 5).

If the temperature $T_0$ of the drum 4 is suitable for use of the data recorder 1, such as −10° C. to 50° C., the waiting state is indicated on the display monitor 9 to display the time during which the data recorder 1 is in the dew formation detecting state (step S5).

After a pre-set time period has passed from powerup, e.g., three minutes, the temperature $T_1$ of the drum 4 is measured by the temperature sensor 8 (step S6).

The environment air temperature $T_E$, which is the ambient temperature of the data recorder 1, is estimated at step S7, using the temperature $T_0$ of the drum 4 on and the temperature $T_1$ of the drum 4 after lapse of a pre-set time as from powerup (step S7). The environment air temperature $T_E$ can be found empirically by the following equation:

$$T_E = 10T_1 - 9T_0 - 41$$

which may be generalized to $$T_E = AT_1 - BT_0 - C.$$

This equation is a generalized equation for calculating the environment temperature which uses a temperature $T_0$ of the drum 4 under measurement on powerup, as measured at step S3, a temperature $T_1$ of the drum under measurement after lapse of a pre-set time after powerup, as measured at step S6, and coefficients A, B which take into account the conditions of the environment inside and outside the electronic equipment, expresses the temperature of the object under measurement as $AT_1$, $BT_0$ and uses a constant C representing the environment temperature $T_E$ when $AT_1$ is equal to $BT_0$. Of course, the values of A, B and C vary with the ambient environment such as temperature or humidity inside and outside the electronic equipment.

The dew point temperature $T_R$ is found from the environment temperature $T_E$ and the humidity $Z_R$ around the electronic equipment (step S8) detected by a humidity detector 10 shown in FIG. 1. The humidity $Z_R$ is a maximum allowable humidity under the operating environment of the data recorder 1. To find the dew point temperature $T_R$, a partial pressure $P_W$ of the water vapor of the environment temperature $T_E$ is first obtained for a constant humidity of 70% by $$P_W = Z_R \cdot P_S$$

where $P_S$ is a saturation vapor pressure as found from the well-known saturation vapor pressure table.

Of course, the partial pressure $P_W$ of the water vapor may be determined by actually measuring the humidity using the humidity detector 10.

Since the dew point temperature $T_R$ is the saturation temperature corresponding to the partial pressure $P_W$ of the water vapor, as found by the above equation, it is found from the well-known saturation vapor table.

Preferably, this dew point temperature TR is set so as to be higher by 1° C. than the dew point temperature as found, in consideration of variations in the temperature sensor 8.

The dew point temperature $T_R$ as found is compared at step S9 to the temperature $T_1$ of the drum after lapse of a pre-set time as from the time of powerup. If it is the temperature $T_1$ of the drum 4 that is the higher, it is verified that there is no dew formation so that the cassette tape operating unit 3 of the data recorder 1 is set to a normal mode where the type is in contact with the drum (step S10) setting the data recorder 1 to a stand-by mode. The display monitor 9 at this time is set to the normal data recorder display mode.

If the temperature $T_1$ of the drum 4 is not higher than the dew point temperature $T_R$ as found, dew formation is verified to have occurred, so that the dew formation indication is made on the display monitor 9 of the data recorder 1, whilst the "WARM WAIT" flashes to indicate that the data recorder is in the warmup state (step S11). If the cassette tape operating unit 3 is set to the unthread mode, the drum 4a and the drum motor are run, thus helping remove the dew drops by air movement and rise in temperature as the drum 4a and the drum motor rotate.

The temperature $T_2$ of the drum 4 then is measured by the temperature sensor 8 (step S12). The temperature $T_2$ of the drum 4 thus found is compared to the dew point temperature $T_R$ (step S13). The process from step S11 to step S13 is repeated until the temperature $T_2$ of the drum 4 is higher than the dew point temperature $T_R$.

As from the time the temperature $T_2$ of the drum 4 is higher than the dew point temperature $T_R$, an optional time length of, for example, ten minutes is set as the drying time of the drum 4 (step S14). The cassette tape operating unit 3 of the data recorder 1 then is set to the normal mode (step S10) to set the data recorder 1 to the stand-by mode.

In the above-described structure of the instant embodiment, dew formation can be optimally predicted by providing the sole temperature sensor 8 in the data recorder 1 for measuring the drum temperature.

In the present embodiment, since only one temperature sensor 8 is provided in the data recorder 1 for measuring the drum temperature and for estimating the environment air temperature, it becomes advantageously possible to save on the space in the data recorder 1.

In the above-described embodiment, the environment air temperature $T_E$ is found by calculations from the temperature $T_0$ of the object under measurement directly after turning on the power source for the drum 4 and the temperature T1 after lapse of three minutes. However, it is also possible to provide a temperature sensor for measuring the environment air temperature $T_E$ at a specified position outside of the data recorder 1. In this case, the temperature of the drum 4 and the environment air temperature $T_E$ can be predicted and measured by the temperature sensor.

If, in conjunction with the above-described embodiment, a dew formation sensor is provided for detecting the dew formation in a temperature area with low possibility of dew formation, whereas, in a temperature area with high possibility of dew formation, the dew formation prediction device employing the temperature sensor 8 of the above-described embodiment is used to predict the dew formation, the time for checking may be shortened in the temperature area with low possibility of dew formation.

If the dew formation sensor is to be provided, it may be provided in a place where dew formation occurs earlier than on the drum 4 due to exposure to environment air. Since the data recorder 1 is of the forced air cooling configuration employing a blower fan, it is sufficient if the dew formation sensor is provided in the vicinity of an air suction opening of the air cooling system.

In the above-described embodiment, the present invention is applied to a data recorder. However, the present invention can naturally be applied to an electronic equipment and to a recording and/or reproducing apparatus having a tape transport system employing the helical scan system, such as a video tape recorder.

Although the embodiment of the present invention directed to a data recorder has been explained in the foregoing, a wide variety of different configurations can be used without departing from the scope of the invention.

What is claimed is:

1. A dew formation prediction apparatus comprising:

object temperature detection means for detecting a temperature of an object provided in an electronic equipment;

environment air temperature acquiring means for acquiring an environment air temperature surrounding the electronic equipment;

means for acquiring a humidity of an operating environment around the electronic equipment;

dew point temperature calculating means for calculating a dew point temperature at the acquired humidity from said environment air temperature; and dew formation occurrence verification means for verifying an occurrence of dew formation when the temperature of said object as acquired by said object temperature detection means is not higher than the calculated dew point temperature.

2. The dew formation prediction apparatus according to claim 1 wherein said environment air temperature acquiring means comprises environment air temperature calculating means which calculates the environment air temperature $T_E$ from $$T_E = AT_1 - BT_0 - C$$

where $T_0$ is a temperature on powerup of the object provided in the electronic equipment as obtained by said object temperature detection means, $T_1$ is the temperature of the object under measurement after lapse of a specified time period from the powerup, A and B are coefficients to compensate for the variations in conditions of an ambient environment inside and outside the electronic equipment and C is a constant representing the environment air temperature $T_E$ when $AT_1$ and $BT_0$, representing the temperatures of the object provided in the electronic equipment when taking into account conditions of an environment inside and outside the electronic equipment, are equal to each other.

3. The dew formation prediction apparatus according to claim 1 wherein, as said environment air temperature acquiring means, there is provided an environment air temperature detecting temperature sensor for detecting the environment air temperature.

4. The dew formation prediction apparatus according to claim 1 wherein said object provided in the electronic equipment is a drum of a tape transport system employing a helical scan system; and wherein a drum temperature on powerup of the electronic equipment having the tape transport system and the drum temperature after lapse of the specified time period after powerup are measured to estimate the environment air temperature.

5. A dew formation prediction method comprising:

detecting a temperature of an object provided in an electronic equipment;

acquiring an environment air temperature of the electronic equipment;

acquiring a humidity of an operating environment around the electronic equipment;

calculating a dew point temperature at the humidity acquired in said step of acquiring from said environment air temperature; and verifying an occurrence of dew formation when the temperature of said object is not higher than the calculated dew point temperature.

6. The dew formation prediction method according to claim 5 wherein said object provided in the electronic equipment is a drum of a tape transport system employing a helical scan system;

measurement is made of a temperature of the drum on powerup of the electronic equipment having said tape operating system and a temperature of the drum after lapse of a specified time after powerup; and wherein the environment air temperature is estimated from the temperature of the drum as measured on powerup and from the drum temperature as measured after lapse of the specified time after powerup.

7. An environment air temperature predicting apparatus comprising:

temperature measurement means for measuring a temperature $T_0$ on powerup of an object under measurement provided in an electronic equipment and a temperature $T_1$ of said object under measurement after lapse of a pre-set time from the powerup; and environment air temperature calculating means for calculating an environment air temperature $T_E$ from $$T_E = AT_1 - BT_0 - C$$

where $T_0$ is the temperature on powerup of the object under measurement as obtained by said temperature measurement means, $T_1$ is the temperature measured after the lapse of the pre-set time from the powerup , A and B are coefficients to compensate for variations in conditions of an ambient environment inside and outside the electronic equipment and C is a constant representing the environment air temperature $T_E$ when $AT_1$ and $BT_0$, representing the temperatures of the object under measurement when taking into account the conditions of the ambient environment inside and outside the electronic equipment, are equal to each other.

8. An environment air temperature prediction method comprising the steps of:

measuring a temperature $T_0$ on powerup of an object under measurement provided in an electronic equipment and a temperature $T_1$ of said object under measurement after lapse of a pre-set time from the powerup; and calculating an environment air temperature $T_E$ from $$T_E = AT_1 - BT_0 - C$$

where $T_0$ is the temperature as measured on powerup of the object under measurement, $T_1$ is the temperature of the object under measurement after the lapse of the pre-set time from the powerup, A and B are coefficients to compensate for variations in conditions of an ambient environment inside and outside the electronic equipment and C is a constant representing the environment air temperature $T_E$ when $AT_1$ and $BT_0$, representing a temperature of the object under measurement when taking into account conditions of an environment inside and outside the electronic equipment, are equal to each other.

9. A temperature predicting system for use in a recording and/or reproducing apparatus of a helical scan system having a tape transport system, comprising:

drum temperature detection means for detecting a temperature of a drum of the tape transport system provided in a main body of the apparatus;

environment air acquisition means for acquiring an environment air temperature around said main body of the apparatus;

means for acquiring a humidity of an operating environment of the apparatus;

dew point temperature calculating means for calculating, from said environment air temperature, a dew point temperature at a humidity which takes into account an operating temperature around said main body of the apparatus; and dew formation occurrence verification means for verifying an occurrence of dew formation when the temperature of the drum as obtained by said drum temperature detection means is not higher than the calculated dew point temperature.

* * * * *